(12) United States Patent  
Yazaki et al.

(10) Patent No.: US 11,501,750 B2  
(45) Date of Patent: Nov. 15, 2022

(54) ULTRASOUND IMAGING DEVICE, ULTRASONIC PROBE, AND TRANSMISSION DEVICE

(71) Applicant: Hitachi, Ltd., Tokyo (JP)

(72) Inventors: Toru Yazaki, Tokyo (JP); Kazuhiro Amino, Tokyo (JP)

(73) Assignee: FUJIFILM HEALTHCARE CORPORATION, Chiba (JP)

( * ) Notice: Subject to any disclaimer, the term of this patent is extended or adjusted under 35 U.S.C. 154(b) by 324 days.

(21) Appl. No.: 16/646,766

(22) PCT Filed: Sep. 26, 2018

(86) PCT No.: PCT/JP2018/035726  
§ 371 (c)(1),  
(2) Date: Mar. 12, 2020

(87) PCT Pub. No.: WO2019/093004  
PCT Pub. Date: May 16, 2019

(65) Prior Publication Data  
US 2020/0289092 A1 Sep. 17, 2020

(30) Foreign Application Priority Data

Nov. 7, 2017 (JP) .............................. JP2017-214908

(51) Int. Cl.  
*H04B 1/02* (2006.01)  
*G10K 11/34* (2006.01)  
(Continued)

(52) U.S. Cl.  
CPC .............. *G10K 11/34* (2013.01); *A61B 8/145* (2013.01); *A61B 8/4444* (2013.01); *A61B 8/54* (2013.01);  
(Continued)

(58) Field of Classification Search  
None  
See application file for complete search history.

(56) References Cited

U.S. PATENT DOCUMENTS 4,293,822 A * 10/1981 McFadyen ........... H03G 3/3005  
330/257  
4,643,028 A * 2/1987 Kondo ................ G01S 15/8918  
367/105  
(Continued)

FOREIGN PATENT DOCUMENTS

EP 2182633 A1 * 5/2010 ......... H03H 11/1217  
EP 3397955 B1 * 5/2021 ........... G01N 29/343  
(Continued)

OTHER PUBLICATIONS

Gao, Zheng. "An integrated high-voltage low-distortion current-feedback linear power amplifier for ultrasound transmitters using digital predistortion and dynamic current biasing techniques." IEEE Transactions on Circuits and Systems II: Express Briefs 61.6 (2014): 373-377 (Year: 2014).*

(Continued)

*Primary Examiner* — Isam A Alsomiri  
*Assistant Examiner* — Jonathan D Armstrong  
(74) *Attorney, Agent, or Firm* — Mattingly & Malur, PC

(57) ABSTRACT

An ultrasonic imaging apparatus includes a plurality of transducers that transmit ultrasonic waves and a transmission unit that supplies drive signals to the plurality of transducers. An amplitude control voltage generation unit and a transmission circuit unit are connected to a common voltage power supply. An amplitude control voltage generation unit receives an output voltage of the voltage power supply and an attenuation degree setting signal instructing an attenuation degree of the drive signal for each of the transducers for weighting of the drive signal, and generates an amplitude control voltage corresponding to a voltage (Continued)

obtained by attenuating the output voltage by the attenuation degree. The output voltage of the voltage power supply is reduced to a voltage corresponding to the amplitude control voltage, and a drive signal having a predetermined waveform is generated whose amplitude is the voltage after the reduction for each of the transducers.

10 Claims, 11 Drawing Sheets

(51) Int. Cl.
  *A61B 8/14* (2006.01)
  *A61B 8/00* (2006.01)
  *G01S 7/28* (2006.01)
(52) U.S. Cl.
  CPC .............. *A61B 8/56* (2013.01); *G01S 7/2813* (2013.01); *G10K 11/348* (2013.01); *A61B 8/4488* (2013.01)

(56) References Cited

U.S. PATENT DOCUMENTS

| | | | | |
|---|---|---|---|---|
| 4,829,491 | A * | 5/1989 | Saugeon | G10K 11/346 367/105 |
| 5,382,916 | A * | 1/1995 | King | H01L 27/0214 330/253 |
| 6,432,055 | B1 * | 8/2002 | Carp | G01S 15/895 600/437 |
| 10,448,923 | B2 | 10/2019 | Nishimoto et al. | |
| 2004/0254459 | A1 * | 12/2004 | Kristoffersen | B06B 1/0215 600/437 |
| 2008/0066552 | A1 * | 3/2008 | Amemiya | H03K 17/6872 73/602 |
| 2012/0111119 | A1 * | 5/2012 | Small | G06F 3/0412 73/633 |
| 2015/0091646 | A1 * | 4/2015 | Shifrin | H03F 3/45183 330/255 |
| 2018/0313792 | A1 * | 11/2018 | Cook | G01N 29/343 |

FOREIGN PATENT DOCUMENTS

| | | | | |
|---|---|---|---|---|
| JP | 01-265945 A | 10/1989 | | |
| JP | 09-234202 A | 9/1997 | | |
| JP | 2006-101997 A | 4/2006 | | |
| WO | WO-9309599 A2 * | 5/1993 | ............. | G05F 3/262 |
| WO | WO-2010055427 A1 * | 5/2010 | ........... | B06B 1/0215 |
| WO | WO-2013110391 A1 * | 8/2013 | ........... | B06B 1/0215 |
| WO | WO-2014005756 A1 * | 1/2014 | ............. | B60R 16/03 |
| WO | 2015/18623 A1 | 2/2015 | | |
| WO | WO-2017114748 A1 * | 7/2017 | ........... | G01N 29/343 |

OTHER PUBLICATIONS

International Preliminary Report on Patentability received in corresponding International Application Mo PCT/JP2018/035726 dated May 12, 2020.
Electronic Industries Association of Japan, Coronal Publishing Co., Ltd., Medical Ultrasound Machines Handbook, Jan. 20, 1997.
International Search Report of PCT/JP2018/035726 dated Nov. 13, 2018.
Chinese Office Action received in corresponding Chinese Application No. 201880055776.X dated Apr. 2, 2022. See notes regarding cited refs. in Corrected NOA.

* cited by examiner

[FIG. 1]
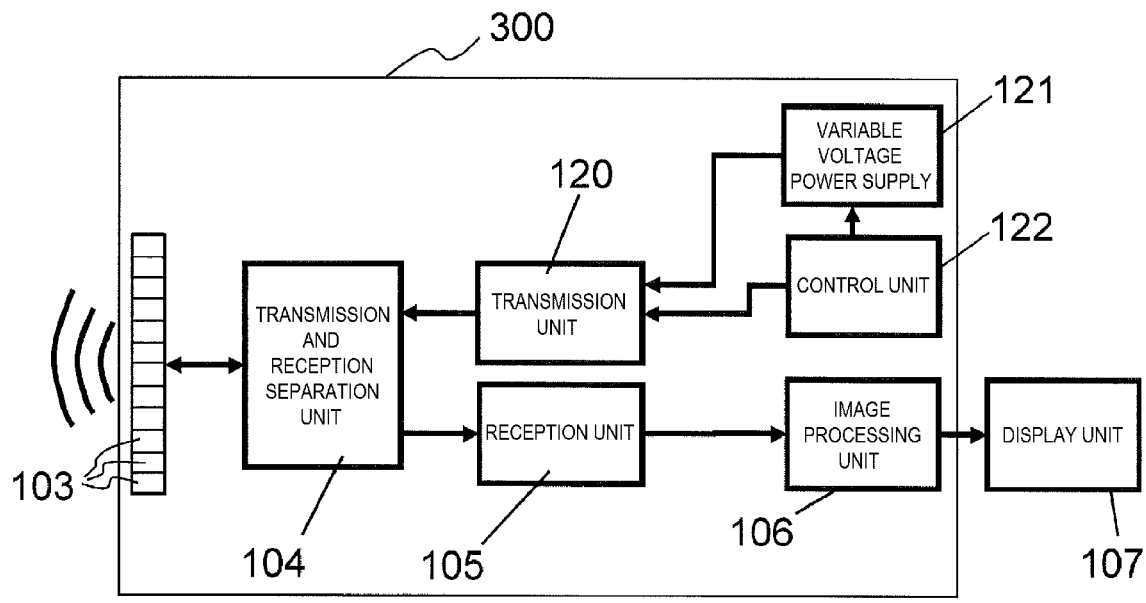
[FIG. 2]
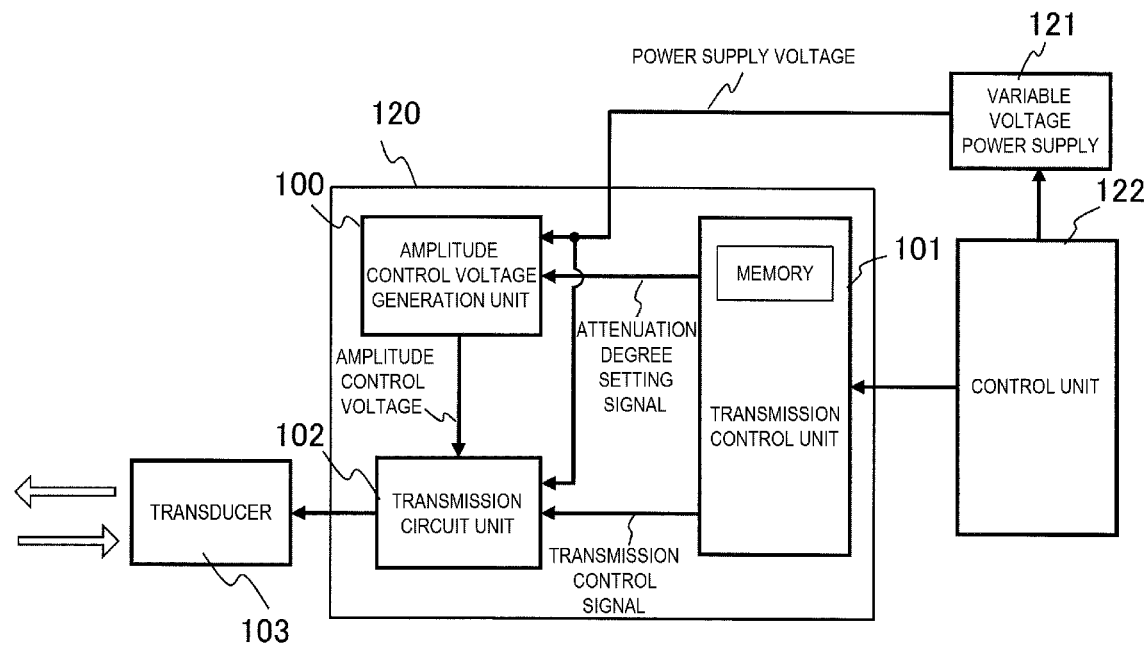

[FIG. 3]
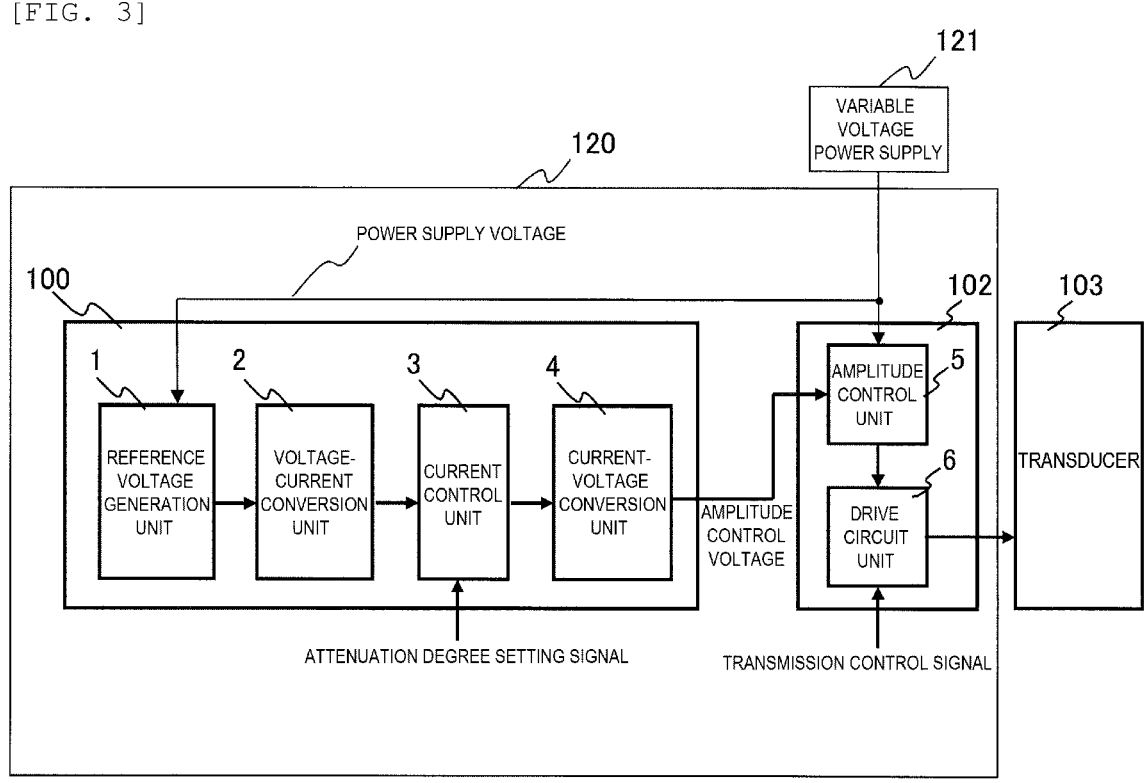

[FIG. 4]
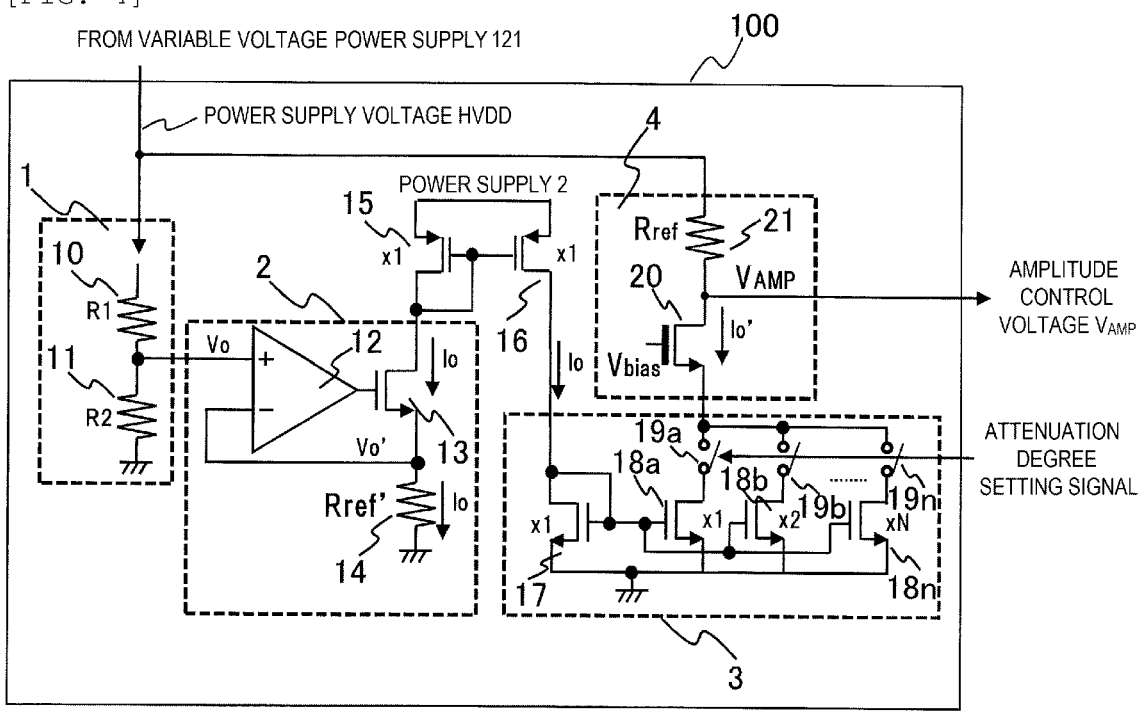

[FIG. 5]
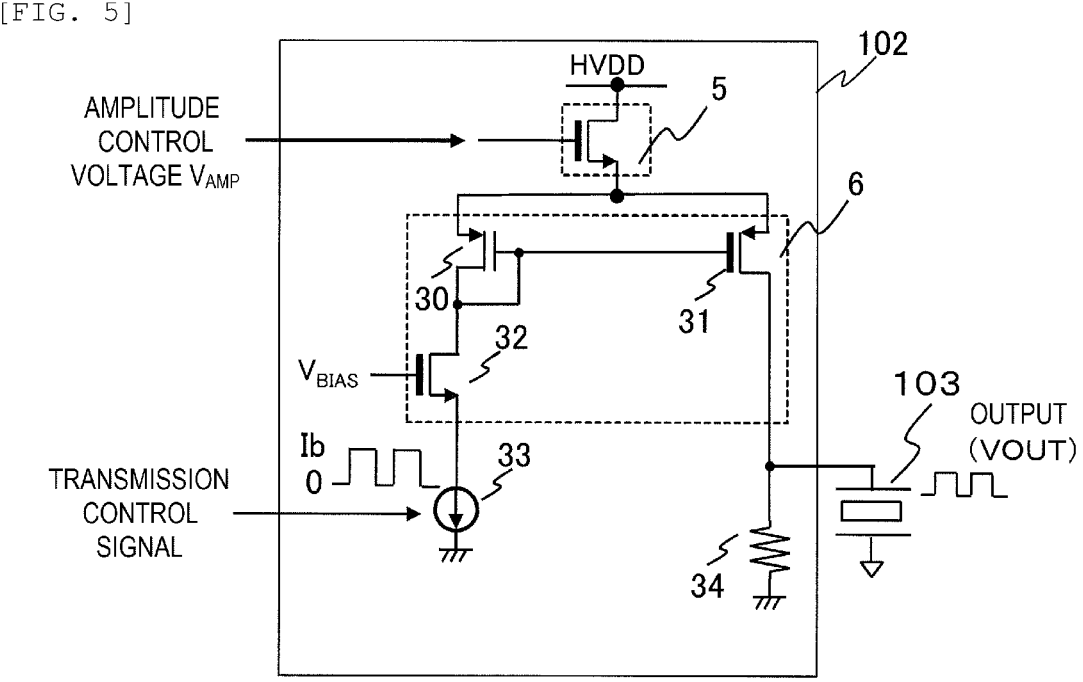

[FIG. 6]
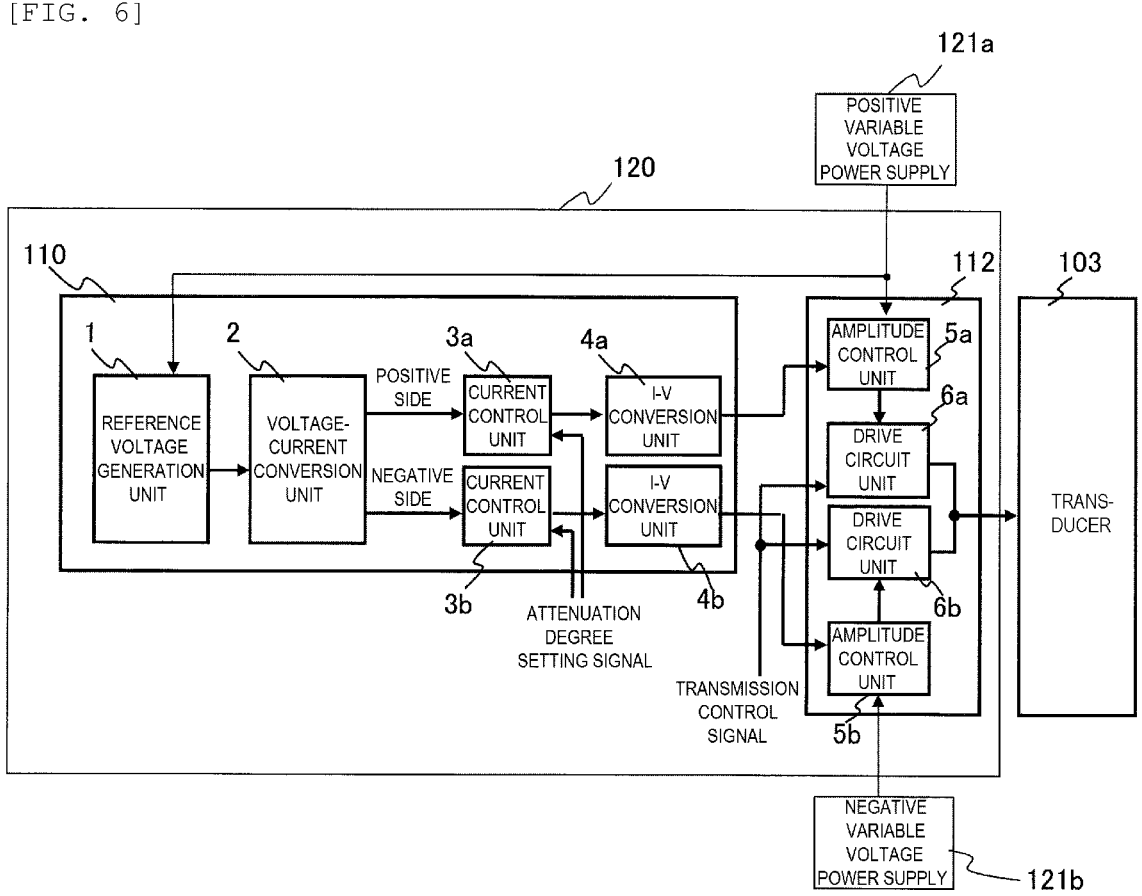

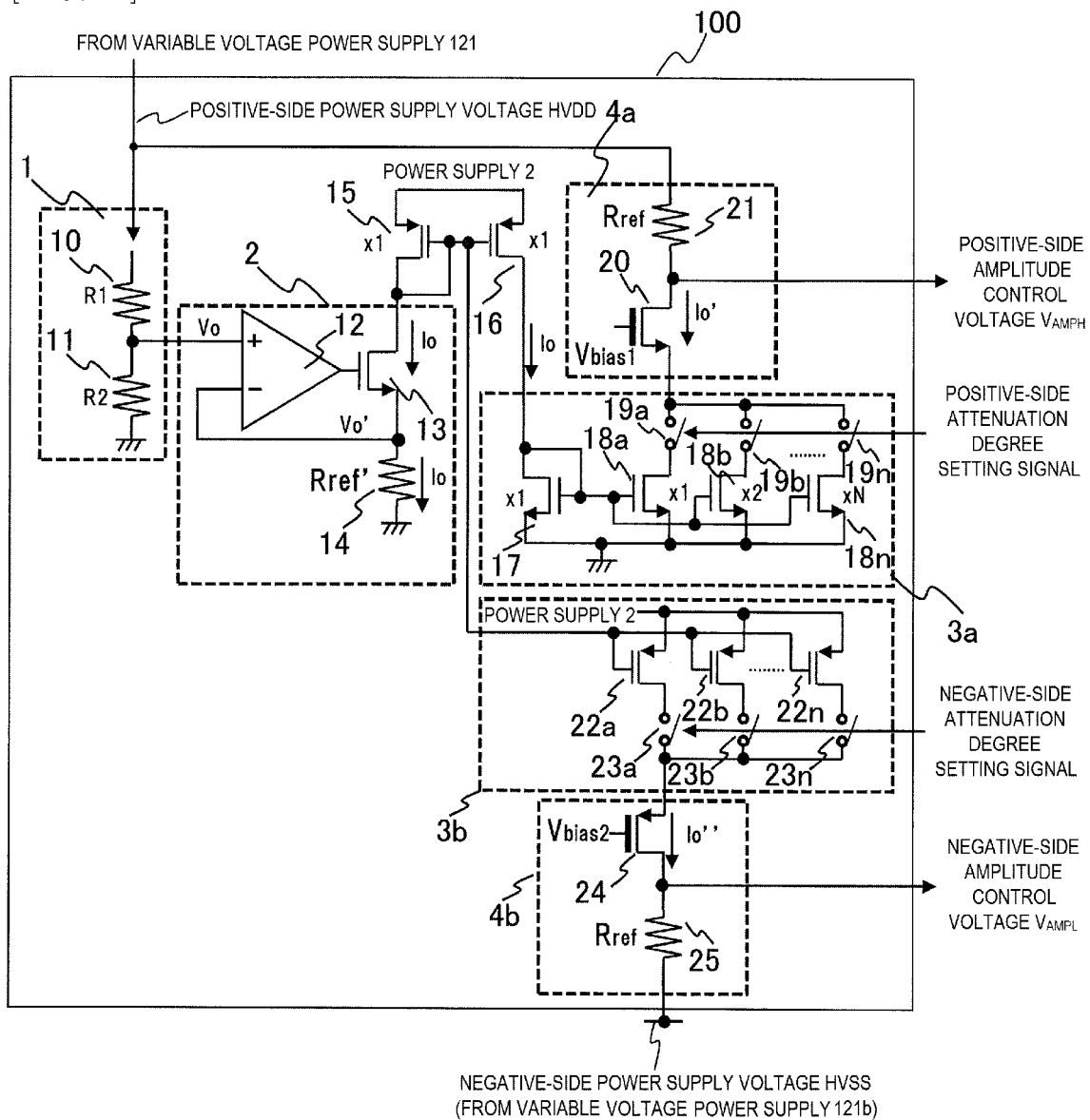
[FIG. 7]

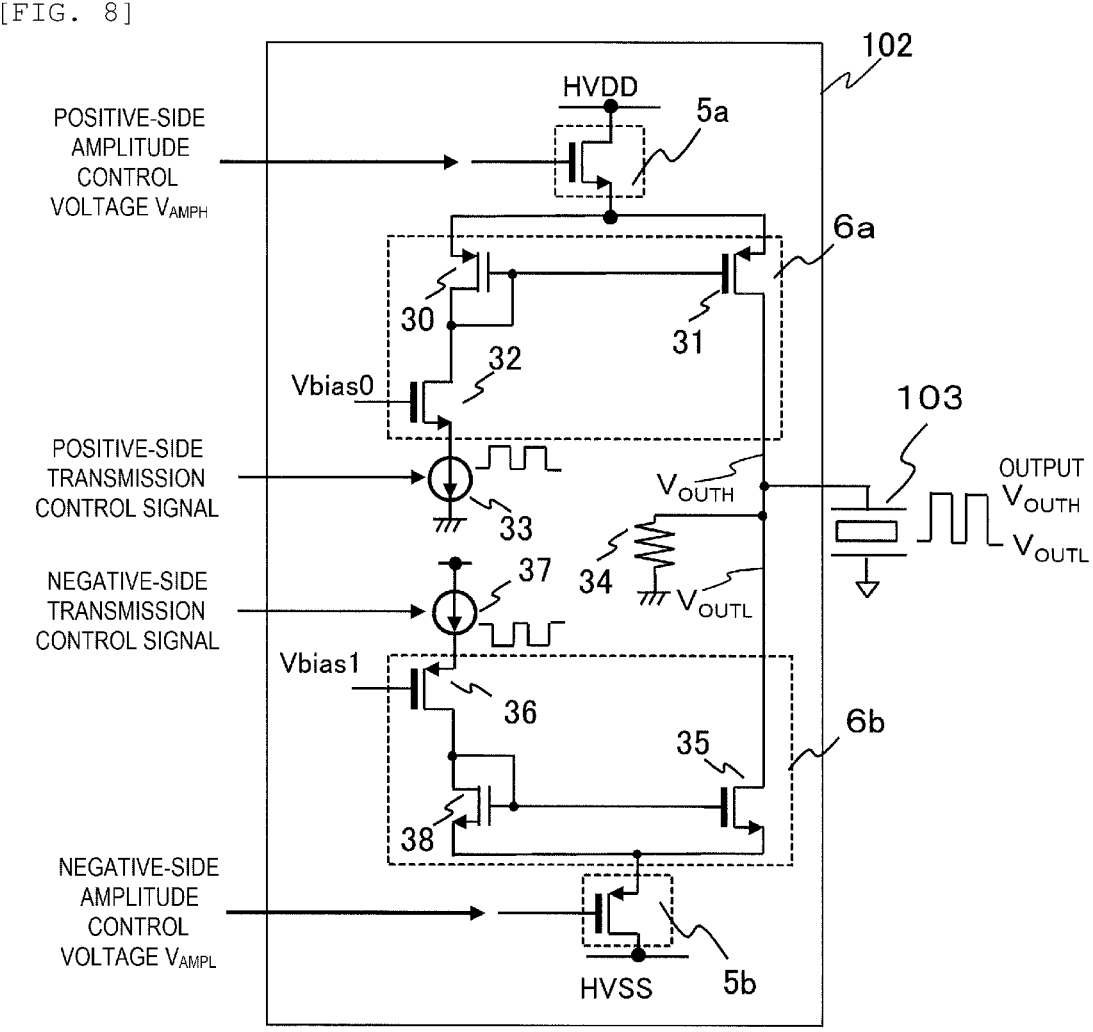
[FIG. 8]

[FIG. 9]
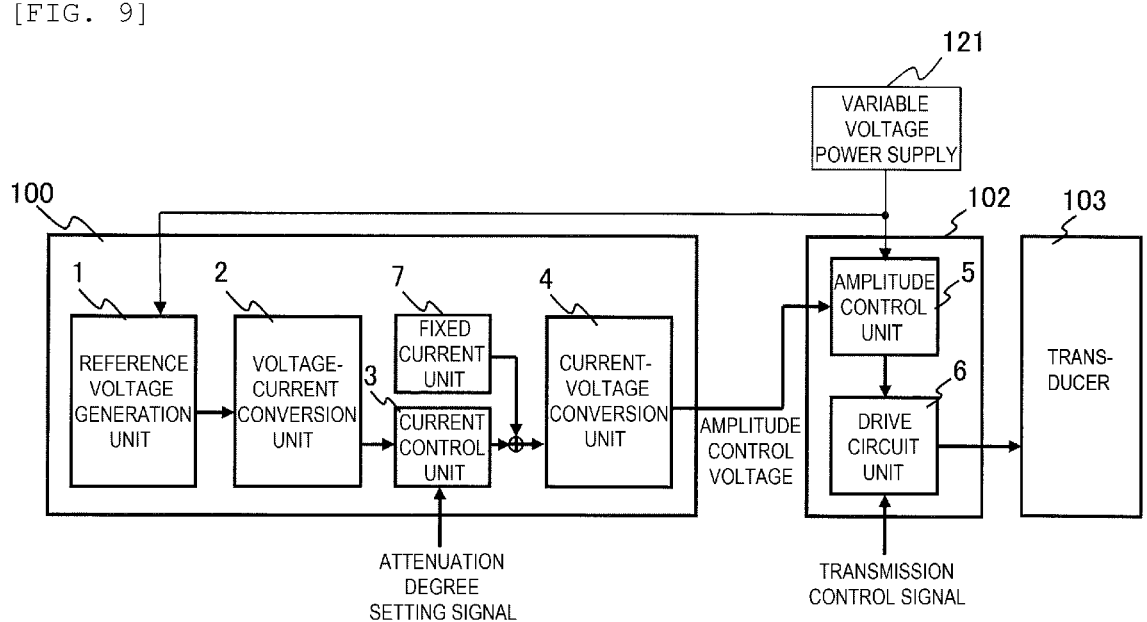
[FIG. 10]
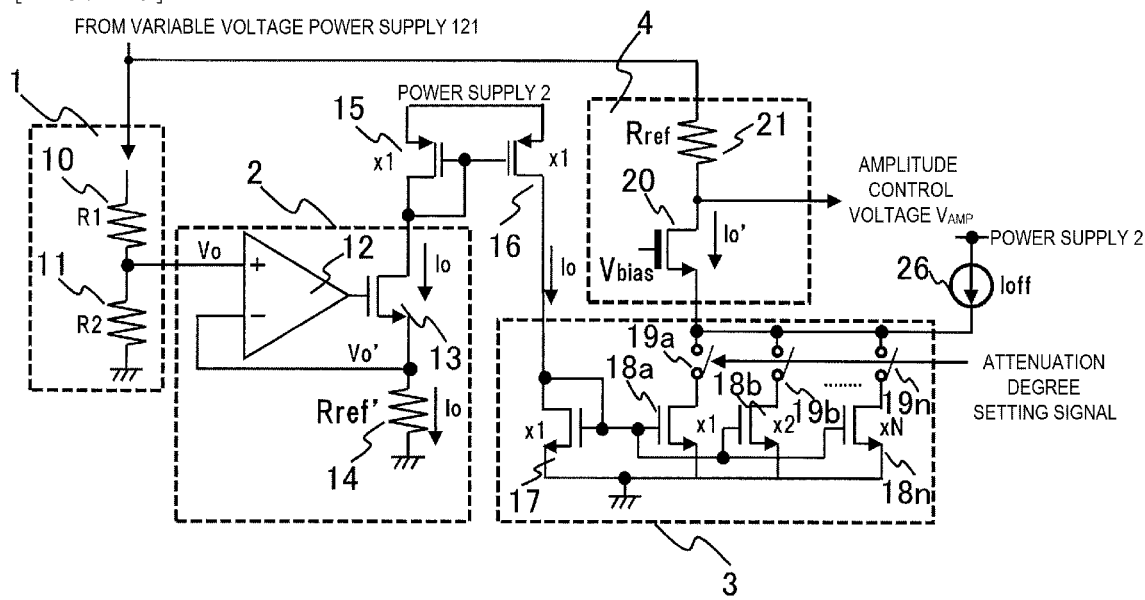

[FIG. 11]
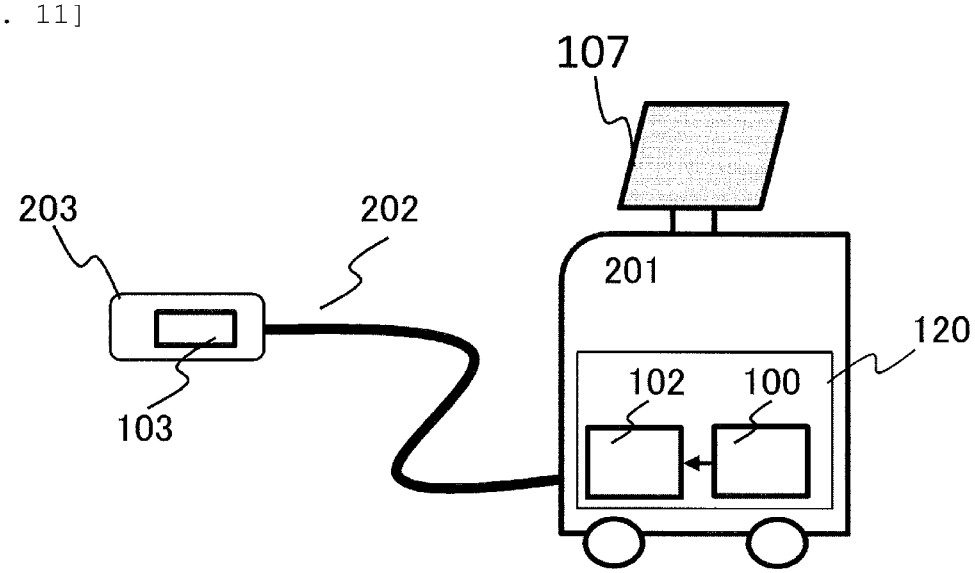
[FIG. 12]
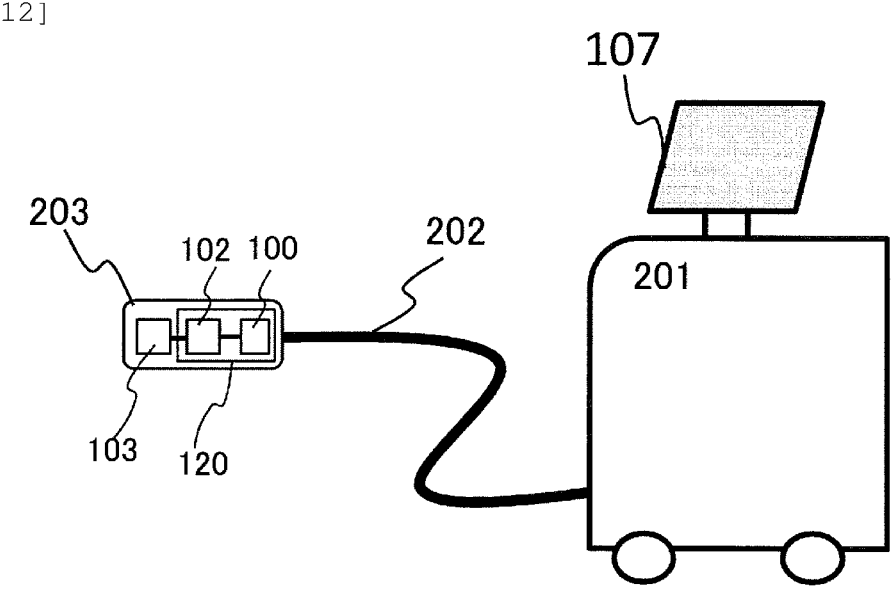

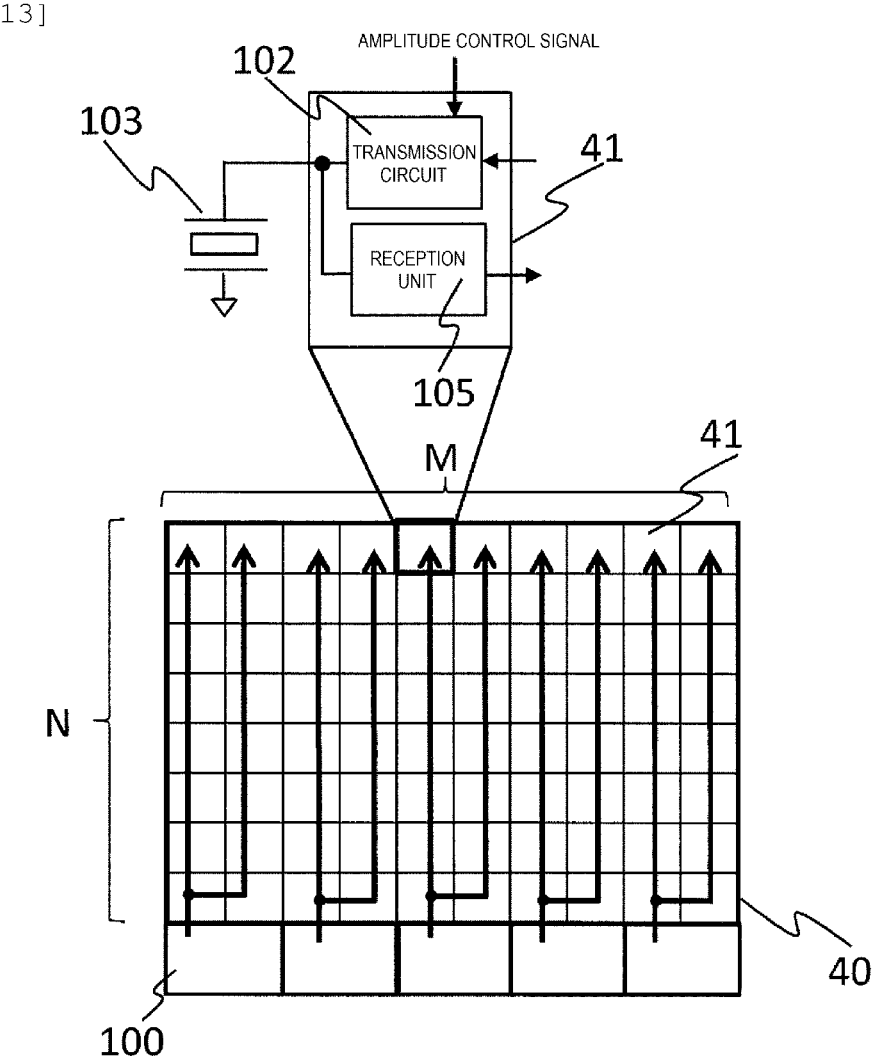
[FIG. 13]

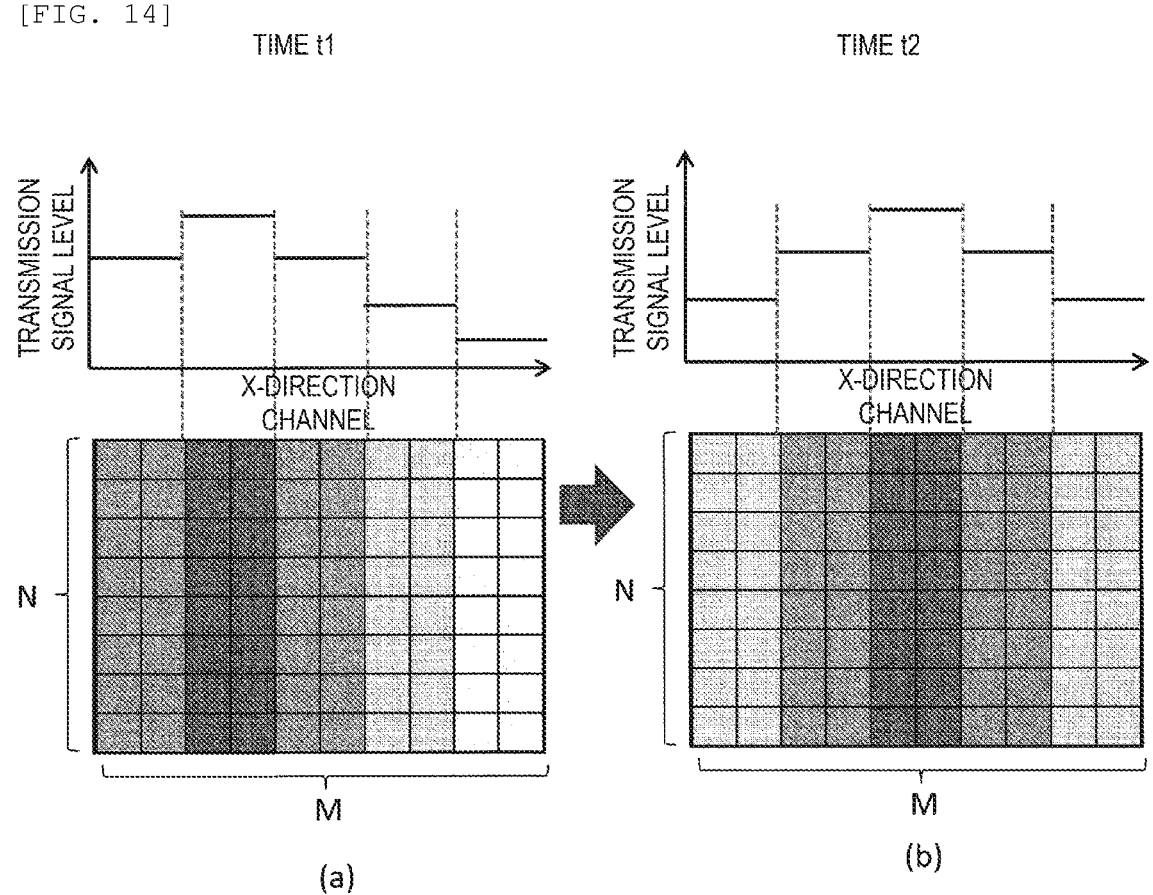
[FIG. 14]

ULTRASOUND IMAGING DEVICE, ULTRASONIC PROBE, AND TRANSMISSION DEVICE

TECHNICAL FIELD

The present invention relates to an ultrasonic imaging apparatus capable of weighting amplitudes of a drive signal.

BACKGROUND ART

An ultrasonic diagnostic apparatus is widely used as a medical diagnosis apparatus that can perform observation non-invasively and in real time. Further, in recent years, in addition to a two-dimensional image in the related art, a three-dimensional stereoscopic image and the like can also be displayed, and the use thereof is steadily increasing. On the other hand, resolution of image quality is lower than that of an X-ray computed tomography (CT) apparatus or a magnetic resonance imaging (MRI) apparatus, and therefore higher image quality is demanded than ever before.

The ultrasonic diagnostic apparatus transmits an ultrasonic beam to a subject from an ultrasonic probe incorporating a plurality of transducers arranged one-dimensionally or two-dimensionally, receives echoes from the subject with a plurality of ultrasonic elements, and generates an ultrasonic image based on the obtained reception signal.

PTL 1 discloses a structure for transmitting an ultrasonic pulse whose amplitude changes in a sine wave shape in a time axis direction in order to reduce a harmonic component included in an ultrasonic beam and to improve image quality of an image obtained by a harmonic echo method. Specifically, a pulse generation circuit is connected to the transducers. The pulse generation circuit changes an amplitude stepwise by sequentially turning on and off a plurality of switching elements connected to a plurality of power supplies having different voltages, generates a pulse signal having an envelope with a sine wave shape, and supplies the pulse signal to an ultrasonic element.

PTL 2 discloses an apparatus including a transmission circuit for supplying a drive signal with a set amplitude to a transducer for each transducer. The transmission circuit is disposed in an ultrasonic probe, and changes a magnitude of the drive signal according to a signal intensity of an amplitude setting signal received from an apparatus main body.

Further, since the ultrasonic diagnostic apparatus is limited to ultrasonic energy that can be radiated to the human body, it is common to change an amplitude of an ultrasonic pulse in the case of imaging a B-mode image and in the case of imaging a color Doppler image in which a plurality of ultrasonic pulses need to be transmitted at the same position. In addition, the amplitude of the ultrasonic pulse needs to be changed depending on a size and a depth of a diagnosis region.

RELATED ART LITERATURE

Patent Literature

PTL 1: JP-A-9-234202
PTL 2: WO 2015/186234 (in particular, paragraphs 0044 to 0050)

SUMMARY OF INVENTION

Technical Problem

In the ultrasonic diagnostic apparatus, in order to obtain a high-quality ultrasonic image, it is desirable to reduce side lobes appearing on both sides of a main lobe of an ultrasonic beam. In order to reduce the side lobes, when a transmission amplitude of a transducer at the center position of the main lobe is set to 100%, it is desired that amplitudes of a drive signal for each transducer are weighted (apodization) so as to gradually reduce the transmission amplitude of the transducer to 80% and 40% as the transducer is away from a transmission center. Further, not only the amplitude is reduced according to a position of the transducer in order to reduce the side lobes, but also weighting according to the arrangement of the transducer is required in order to avoid the occurrence of a grating lobe.

When the ultrasonic beam scanning is performed while weighting the amplitudes to reduce the side lobes, it is necessary to change the weight of the amplitudes of the drive signal of each transducer every time a position or direction of the main lobe is shifted.

Further, when the amplitude of the ultrasonic pulse is changed in order to switch between B-mode imaging and color Doppler imaging, if a position of the ultrasonic pulse does not change, a weighting ratio itself does not need to be changed. However, since the amplitude of the ultrasonic pulse itself is changed, it is necessary to change the amplitude of the drive signal of each transducer. In particular, in the case of an imaging method of alternately transmitting an ultrasonic beam for the B-mode imaging and the color Doppler imaging in one second and simultaneously displaying both images, it is necessary to change a transmission amplitude of the same transducer several times per second.

As a configuration for weighting the amplitudes of the drive signal for each transducer, for example, as in PTL 1, a technique of preparing a plurality of types of power supply voltages and selecting a power supply voltage may be applied. However, in the technique, a wiring that connects the plurality of types of power supply voltages for each transducer and a switch that selects any of the plurality of types of power supply voltages according to the weighted amplitude for each power supply voltage are required. Therefore, circuit scale of a generation circuit of the drive signal increases. Further, a calculation unit that calculates the weighted amplitude for each transducer each time the ultrasonic beam is transmitted, and a control unit that determines which power supply voltage should be selected and turns on the switch are also required.

Further, as in the transmission circuit described in PTL 2, it is also conceivable to apply a technique of changing a magnitude of the drive signal according to a magnitude of an amplitude setting signal received from the apparatus main body, thereby weighting the amplitudes of the drive signal for each transducer. However, even in the case of applying this technique, each time the B-mode imaging and the color Doppler imaging are switched, and each time the ultrasonic beam scanning is performed, required is a calculation unit that calculates an appropriately weighted amplitude magnitude for each transducer, generates an amplitude setting signal having the magnitude as a signal intensity and outputs the amplitude setting signal to the transmission circuit of each transducer.

In this way, when attempting to weight the drive signal for each transducer in order to reduce the side lobes by applying the technique of PTL 1, the circuit scale of the switch, the wiring, and the like increases. In both PTLs 1 and 2, a calculation unit that calculates the weighted amplitude for each transducer, a control unit, and the like are required, and a scale of a calculation processing unit is also increased. Therefore, a problem arises in that the size of an ultrasonic imaging apparatus increases.

An object of the invention is to perform weighting for a drive signal for each transducer without re-calculating an amplitude of the drive signal for each transducer even when an intensity of an ultrasonic beam is changed.

Solution to Problem

In order to achieve the above object, the invention provides the following ultrasonic imaging apparatus. That is, an ultrasonic imaging apparatus of the invention includes a plurality of transducers that transmit ultrasonic waves and a transmission unit that supplies drive signals to the plurality of transducers. The transmission unit includes an amplitude control voltage generation unit and a transmission circuit unit. The amplitude control voltage generation unit and the transmission circuit unit are connected to a common voltage power supply. The amplitude control voltage generation unit receives an output voltage of the voltage power supply and an attenuation degree setting signal instructing an attenuation degree of the drive signal for each of the transducers for weighting for the drive signal, and generates an amplitude control voltage corresponding to a voltage obtained by attenuating the output voltage of the voltage power supply by the attenuation degree. The transmission circuit unit reduces an absolute value of the output voltage of the voltage power supply to a value corresponding to the amplitude control voltage, and generates a drive signal having a predetermined waveform whose amplitude is the voltage after the reduction for each of the transducers.

Advantageous Effect

According to the invention, even when the intensity of the ultrasonic beam is changed, the weighting for each transducer can be performed without re-calculating the amplitude of the drive signal for each transducer.

Problems, configurations, and effects other than those described above will become apparent from the following description of the embodiments.

BRIEF DESCRIPTION OF DRAWINGS

FIG. 1 is a block diagram showing an overall configuration of an ultrasonic imaging apparatus according to an embodiment of the invention.

FIG. 2 is a block diagram showing a configuration of a transmission unit 120 of the ultrasonic imaging apparatus of FIG. 1.

FIG. 3 is a block diagram showing a more detailed configuration of the transmission unit 120 of FIG. 2.

FIG. 4 is a circuit diagram of an amplitude control voltage generation unit 100 of the ultrasonic imaging apparatus according to a first embodiment.

FIG. 5 is a circuit diagram of a transmission circuit unit 102 of the ultrasonic imaging apparatus according to the first embodiment.

FIG. 6 is a block diagram showing a configuration of the transmission unit 120 of an ultrasonic imaging apparatus according to a second embodiment.

FIG. 7 is a circuit diagram of the amplitude control voltage generation unit 100 of the ultrasonic imaging apparatus according to the second embodiment.

FIG. 8 is a circuit diagram of the transmission circuit unit 102 of the ultrasonic imaging apparatus according to the second embodiment.

FIG. 9 is a block diagram showing a configuration of the transmission unit 120 of an ultrasonic imaging apparatus according to a third embodiment of the invention.

FIG. 10 is a circuit diagram showing a configuration of the amplitude control voltage generation unit 100 of the ultrasonic imaging apparatus according to the third embodiment.

FIG. 11 is a block diagram showing an appearance of an ultrasonic diagnostic apparatus according to a fourth embodiment of the invention.

FIG. 12 is a block diagram showing an appearance of an ultrasonic diagnostic apparatus according to a fifth embodiment of the invention.

FIG. 13 is an explanatory diagram showing an arrangement of an analog front end circuit 41 connected to a transducer 103 according to the fourth and fifth embodiments.

FIGS. 14(a) and 14(b) are explanatory diagrams showing distribution of transmission signal levels (amplitudes) of the transducer 103 according to the fourth and fifth embodiments at times t1 and t2.

DESCRIPTION OF EMBODIMENTS

In the following embodiments, description may be divided into a plurality of sections or embodiments if necessary for convenience. Unless particularly specified, these embodiments are not independent with each other, but in a relationship in which one embodiment is a variation, detailed description, supplementary description, or the like of a part or all of another embodiment. In the following embodiments, when the number and the like (including number of article, numeric value, quantity, or range) of an element are referred to, these parameters are not limited to the specific numbers, and the values may be greater or less than these specific numbers, unless particularly specified or unless the specific numbers are apparently limited to specific numbers in principle.

Further, in the following embodiments, it is needless to say that the constituent elements (including element steps) are not necessarily essential, unless particularly specified or considered to be apparently essential in principle. Similarly, in the following embodiments, when referring to shapes, positional relationships, and the like of the constituent elements and the like, shapes and the like which are substantially approximate or similar to those are included, unless particularly specified or considered to be apparently excluded in principle. The same also applies to the numeric value and the ranges described above.

Hereinafter, an ultrasonic imaging apparatus according to embodiments will be described with reference to the drawings. In all the drawings for illustrating the embodiments, the same configuration are denoted by the same reference numerals in principle, and the repetitive description thereof will be omitted.

FIG. 1 shows an example of a schematic configuration of an ultrasonic imaging apparatus according to the present embodiment. FIG. 2 shows a configuration of a transmission unit 120. As shown in FIGS. 1 and 2, an ultrasonic imaging apparatus 300 of the present embodiment includes a plurality of transducers 103 that transmit ultrasonic waves, and the transmission unit 120 that supplies drive signals to each of the plurality of transducers 103. The transmission unit 120 includes an amplitude control voltage generation unit 100 and a transmission circuit unit 102. The amplitude control voltage generation unit 100 and the transmission circuit unit 102 are connected to a common voltage power supply 121.

The amplitude control voltage generation unit 100 receives an output voltage of the voltage power supply 121 and an attenuation degree setting signal instructing an attenuation degree of a drive signal for each transducer 103, and generates an amplitude control voltage corresponding to a voltage obtained by attenuating the output voltage of the voltage power supply 121 by the attenuation degree indicated by the attenuation degree setting signal.

The transmission circuit unit 102 reduces an absolute value of the output voltage of the voltage power supply 121 to a value corresponding to the amplitude control voltage, and generates a drive signal having a predetermined waveform whose amplitude is the voltage after the reduction for each transducer. The generated drive signal is output to each transducer 103.

In this way, in the present embodiment, the attenuation degree for each transducer indicated by the attenuation degree setting signal is received, and the amplitude control voltage corresponding to the voltage obtained by attenuating the output voltage of the voltage power supply 121 by the attenuation degree is generated for each transducer, so that amplitudes of the drive signal can be weighted. Thus, by setting the attenuation degree according to the position of the transducer, for example, by gradually increasing the attenuation degree as the transducer is away from the at the center without attenuating the transducer at the center of the ultrasonic beam, the amplitudes of the drive signal can be weighted according to the position of the transducer while reducing or increasing an overall output of the ultrasonic beam by simply changing the output voltage of the voltage power supply 121.

Accordingly, an output of each transducer can be weighted, for example, gradually decreasing the output as the transducer is away from the center of an ultrasonic beam while changing the output of the ultrasonic beam according to the change of an imaging mode, so that side lobes of the ultrasonic beam can be prevented.

In the present embodiment, even when the intensity of the ultrasonic beam is changed by changing the imaging mode a plurality of times in one second, unlike the related art, it is not necessary to calculate an attenuated (weighted) amplitude voltage for every change or set an amplitude setting signal, and only a power supply voltage should be changed. Therefore, it is possible to reduce a scale of the calculation circuit and the control circuit and the number of cables, and to provide an ultrasonic imaging apparatus having a small size and a simple configuration.

When weight distribution is changed according to the position of the transducer, for example, in the case of ultrasonic beam scanning, an attenuation degree setting signal instructing the attenuation degree for each transducer may be changed, and it is not necessary to calculate the attenuated amplitude voltage.

The transmission circuit unit 102 and the amplitude control voltage generation unit 100 may be disposed for each transducer 103.

A transmission control unit 101 that generates an attenuation degree setting signal for each transducer 103 and outputs the signal to the amplitude control voltage generation unit 100 may be disposed in the transmission unit 120.

Hereinafter, the ultrasonic imaging apparatus of the present embodiment will be described in more detail.

First Embodiment

An ultrasonic imaging apparatus according to a first embodiment of the invention will be described in detail.

As shown in FIG. 1, the ultrasonic imaging apparatus 300 according to the first embodiment includes a reception unit 105, a transmission and reception separation unit 104, a control unit 122, and an image processing unit 106 in addition to the plurality of transducers 103, the transmission unit 120, and the voltage power supply 121. The voltage power supply 121 is a variable voltage power supply capable of changing a voltage to be output.

As to be described in detail below, the transmission unit 120 generates a drive signal weighted for each transducer 103 from a voltage supplied from the variable voltage power supply 121, outputs the drive signal to the transducer 103, and causes the transducer 103 to transmit an ultrasonic beam to an imaging region of a subject (not shown). An intensity of the ultrasonic beam is changed depending on an imaging mode. When the imaging mode is simultaneous imaging of a B-mode and a color Doppler, an ultrasonic beam having an intensity set for each imaging is alternately emitted. The ultrasonic beam is reflected by the tissue of the subject to generate an echo, and the echo is received by each transducer 103 of a probe 130. The control unit 122 controls the transmission unit 120 and the variable voltage power supply 121.

When the imaging mode is the B-mode, the reception unit 105 performs a processing of adding after delaying a reception signal output from each transducer 103 (reception beamforming) so as to generate focus data for a plurality of reception focuses set in the imaging region. When the imaging mode is the color Doppler, the reception unit 105 calculates a Doppler frequency for each reception focus by using a signal obtained by transmitting and receiving the ultrasonic wave for a plurality of times in order to obtain blood flow information. When the imaging mode is the B-mode, the image processing unit 106 generates a B-mode image of the imaging region by setting a value of focus data of the reception focus to a pixel value of a pixel at a position of the reception focus. When the imaging mode is the color Doppler, the image processing unit 106 assigns a color corresponding to the Doppler frequency to the pixel at the position of the reception focus, and generates a color Doppler image. When the imaging mode is both the B-mode and the color Doppler, both images are generated. The generated image is displayed on a display unit 107 connected to the image processing unit 106.

The transmission and reception separation unit 104 separates the drive signal output from the transmission unit 121 to the transducer 103 and the reception signal output by the transducer 103.

The transmission unit 120 will be described in more detail. As shown in FIG. 2, the transmission unit 120 includes a transmission control unit 101 in addition to the amplitude control voltage generation unit 100 that generates the amplitude control voltage and the transmission circuit unit 102. The amplitude control voltage generation unit 100 and the transmission circuit unit 102 are disposed for each transducer 103. The amplitude control voltage generation unit 100 and the transmission circuit unit 102 are both connected to the common variable voltage power supply 121. The transmission control unit 101 generates an attenuation degree setting signal and a transmission control signal, and outputs the signals to the amplitude control voltage generation unit 100 and the transmission circuit unit 102.

FIG. 3 shows structures of the amplitude control voltage generation unit 100 and the transmission circuit unit 102.

The amplitude control voltage generation unit 100 includes a reference voltage generation unit 1 that generates a reference voltage from an output voltage of the voltage power supply 121, a voltage-current conversion unit 2 that converts the reference voltage into a current, a current control unit that sets the current obtained by conversion of the voltage-current conversion unit 2 according to an attenuation degree setting signal, and a current-voltage conversion unit 4 that generates an amplitude control voltage by converting the current set by the current control unit 3 into a voltage. The transmission circuit unit 102 includes an amplitude control unit 5 that reduces the output voltage of the variable voltage power supply to a voltage corresponding to the amplitude control voltage, and a drive circuit unit 6 that generates a drive signal of a predetermined pulse waveform whose amplitude is the voltage after the reduction. At this time, even when the voltage of the variable voltage power supply 121 is fluctuated, the amplitude control voltage is a voltage proportional to the power supply voltage in which the power supply voltage is attenuated by an attenuation degree indicated by the attenuation degree setting signal, so that amplitude control reflecting the magnitude of the power supply voltage and the attenuation degree (weighting) can be performed. In the present embodiment, each of the above units 1 to 6 is constituted by, for example, an analog circuit.

A specific circuit configuration example of the amplitude control voltage generation unit 100 is shown in FIG. 4.

The reference voltage generation unit 1 has a configuration in which a resistor 10 having a resistance value $R_1$ and a resistor 11 having a resistance value $R_2$ are connected in series, and an output terminal is connected to a wiring between the resistor 10 and the resistor 11. The resistor 10 is connected to the variable voltage power supply 121. When the voltage of the variable voltage power supply 121 is expressed as HVDD, a reference voltage $V_0$ obtained by resistance-dividing the power supply voltage HVDD is output from the output terminal as in the following Formula (1).

$$V_0 = \text{HVDD} \times R_2/(R_1+R_2) \tag{1}$$

The voltage-current conversion unit 2 includes an operational amplifier (OPAMP) 12, an N-type MOS (NMOS) transistor 13, and a reference resistor 14 having a resistance value $R_{ref}'$. The reference voltage $V_0$ output from the reference voltage generation unit 1 is input to a plus terminal of the OPAMP 12. The output of the OPAMP 12 is connected to a gate terminal of the NMOS transistor 13. A source terminal of the NMOS transistor 13 is connected to the reference resistor 14 and a minus terminal of the OPAMP 12 to form a feedback loop. The other terminal of the reference resistor 14 is grounded. An output of the voltage-current conversion unit 2 having such a circuit configuration serves as a drain terminal of the NMOS transistor 13.

With the feedback loop, a voltage $V_0'$ of the minus terminal of the OPAMP 12 is equal to the reference voltage $V_0$, which is an input signal of the plus terminal. Since the voltage $V_0'$ is also connected to the reference resistor 14, a current $I_0$ flowing through the reference resistor 14 is $I_0 = V_0'/R_{ref}'$. Therefore, the current $I_0$ is expressed by Formula (2), and is output as an output of the voltage-current conversion unit 2 from the drain terminal of the NMOS transistor 13.

$$I_0 = V_0/R_{ref}' \tag{2}$$

PMOS transistors 15 and 16 are disposed between the voltage-current conversion unit 2 and the current control unit 3. The PMOS transistors 15 and 16 constitute a current mirror circuit, which converts a direction of the output current $I_0$ of the voltage-current conversion circuit 2 and transmits the current to the current control unit 3 in the next stage.

The current control unit 3 includes a current mirror circuit including an NMOS transistor 17 and a plurality of NMOS transistors 18a to 18n, and switches 19a to 19n respectively connected to the NMOS transistors 18a to 18n. In the circuit configuration of FIG. 4, when the same gate voltage is applied, the NMOS transistors 18a to 18n include the NMOS transistor 18a through which a current having the same magnitude (amplification factor 1) as the NMOS transistor 17 flows, the NMOS transistor 18b through which a current twice (amplification factor 2) that of the NMOS transistor 17 flows, . . . , and the NMOS transistor 18n through which a current of N times (amplification factor N) that of the NMOS transistor 17 flows. Thus, the transmission control unit 101 selectively turns on one or more switches among the switches 19a to 19n according to an attenuation amount setting signal to turn on one or more of the NMOS transistors 18a to 18n. A current $I_0'$, which is a sum of currents flowing through the NMOS transistors that are turned on, is output from the NMOS transistors 18a to 18n as an output of the current control unit 3. Therefore, the current $I_0$ which is an input signal to the current control unit 3 is amplified to the current $I_0'$ and output. When a sum of amplification factors of the NMOS transistors 18a to 18n connected to one or more switches turned on according to the attenuation amount setting signal is n, the amplified current $I_0'$ is expressed by the following Formula (3).

$$I_0' = n \times I_0 \tag{3}$$

The current-voltage conversion unit 4 has a circuit configuration in which a reference resistor 21 having a resistance value $R_{ref}$, connected to the variable voltage power supply 121, and a high-voltage NMOS transistor 20 are connected in series, and the input current $I_0'$ is input to a source terminal of the NMOS transistor 20. An output terminal of an amplitude control voltage is connected to a wiring between the reference resistor 21 and the NMOS transistor 20. The high-voltage NMOS transistor 20 is a protection level shifter of the current control unit 3. The output voltage HVDD of the variable voltage power supply 121 decreases in response to the input current $I_0'$, and an amplitude control voltage $V_{AMP}$ expressed by the following Formula (4) is output from the current-voltage conversion unit 4.

$$V_{AMP} = \text{HVDD} - R_{ref} \times I_0' \tag{4}$$

Substituting Formulas (1) to (3) into Formula (4), Formula (5) is obtained.

$$V_{AMP} = \text{HVDD}(1 - R_{ref}/R_{ref}' \times n \times R_2/(R_1+R_2)) \tag{5}$$

In the Formula (5), when $R_{ref} = R_{ref}'$, the Formula (5) is expressed by the following Formula (6).

$$V_{AMP} = \text{HVDD}(1 - n \times R_2/(R_1+R_2)) \tag{6}$$

As is apparent from the Formula (6), the amplitude control voltage $V_{AMP}$ is a voltage value obtained by attenuating the output voltage HVDD of the variable voltage power supply 121 at a ratio ($n \times R_2/(R_1+R_2)$) proportional to the sum n of the amplification factors of the NMOS transistors 18a to 18n connected to one or more switches turned on according to the attenuation amount setting signal, and even when the output voltage HVDD of the variable voltage power supply 121 fluctuates, the ratio of attenuation ($n \times R_2/(R_1+R_2)$) does not change. For example, when $R_2$ is 10 kΩ and $R_1$ is 90 kΩ in the circuit of FIG. 4, the Formula (6) becomes the following Formula (7).

$$V_{AMP} = \text{HVDD}(1 - 0.1n) \tag{7}$$

In the Formula (7), when n is 1, $V_{AMP}$=0.9 HVDD, and when n is 2, $V_{AMP}$=0.8 HVDD, and the attenuation ratio of the amplitude control voltage $V_{AMP}$ becomes large. Even when the power supply voltage HVDD changes, the attenuation ratio does not change unless the sum n of the amplification factors set according to the attenuation degree setting signal is changed, and the amplitude control voltage $V_{AMP}$ in which the fluctuating power supply voltage HVDD is attenuated by the set attenuation degree can be generated.

Next, a circuit configuration example of the transmission circuit unit 102 will be described with reference to FIG. 5. As shown in FIG. 5, the transmission circuit unit 102 includes the amplitude control unit 5 and the drive circuit unit 6.

The amplitude control unit 5 is formed of a high-voltage NMOS transistor, and the amplitude control voltage $V_{AMP}$ is input to a gate terminal thereof.

The drive circuit unit 6 includes a PMOS transistor 30 and a high-voltage PMOS transistor 31 constituting a current mirror circuit, and a high-voltage NMOS transistor 32 connected to a source terminal of the PMOS transistor 30. A source terminal of the high-voltage NMOS transistor 32 is connected to a current source 33 that outputs a current signal in which two values including zero and a predetermined drive current Ib are alternately output. The transducer 103 and a load resistor 34 are connected to a drain terminal of the high-voltage PMOS transistor 31. The high-voltage NMOS transistor 32 is disposed to protect a withstand voltage of the current signal 33.

A transmission control signal output from the transmission control unit 101 is added to the current source 33. When the transmission control signal is added, the current source 33 outputs the drive current Ib. The drive circuit unit 6 outputs the current signal output from the current source 33 to the transducer 103 as a drive current, and drives the transducer 103. When the voltage of the transducer 103 is $V_{OUT}$ and the drive current is zero, the load resistor 34 discharges an electric charge of the transducer 103, and changes a potential of the transducer 103 to a ground level.

A High level voltage value of the output signal $V_{OUT}$ to the transducer 103 from the drive circuit unit 6 changes in conjunction with the amplitude control voltage $V_{AMP}$. Since the amplitude control voltage $V_{AMP}$ is a voltage obtained by attenuating the power supply voltage HVDD by the set attenuation degree, the output signal $V_{OUT}$ to the transducer 103 also has an amplitude corresponding to the amplitude control voltage $V_{AMP}$. Accordingly, since an ultrasonic signal output from the transducer 103 has an intensity corresponding to the amplitude control voltage $V_{AMP}$, the intensity is weighted by attenuating the drive signal $V_{OUT}$ with a predetermined attenuation degree.

In order to focus the ultrasonic beam at a transmission focus, it is necessary to delay the drive signal for each transducer 103 according to the position of the transmission focus. Therefore, the transmission control unit 101 outputs the transmission control signal at a timing delayed according to the position of the transmission focus.

Therefore, when the intensity of the ultrasonic beam transmitted from the plurality of transducers 103 is changed, it is possible to perform weighting for each transducer only by changing the power supply voltage HVDD without calculating the amplitude of the drive signal for each transducer. For example, by setting the output of the transducer located at the center of the ultrasonic beam to 100% and reducing the output of the transducer as it is away from the center, an ultrasonic beam with reduced side lobes can be transmitted.

At this time, the control unit 122 scans (moves) the position of the ultrasonic beam for each transmission as necessary. Accordingly, since the position of the transducer 103 at the center of the ultrasonic beam is shifted, it is necessary to set the attenuation degree setting signal according to the attenuation degree of the transducer. The transmission control unit 101 receives information for defining a center position of the ultrasonic beam and the attenuation degree of each transducer 103 at that time from the control unit 122 in advance and stores the information in a memory 101a incorporated therein. When receiving an instruction to scan (move) the center position of the ultrasonic beam from the control unit 122, the transmission control unit 101 reads the attenuation degree for each transducer 103 from the memory 101a, generates an attenuation degree setting signal indicating the attenuation degree, and sets an amplitude control voltage in the amplitude control voltage generation unit 100 of each transducer 103.

The control unit 122 controls the variable voltage power supply 121 to fluctuate the voltage HVDD according to the imaging mode when switching the imaging mode as in the B mode and the color Doppler. Specifically, for example, a voltage for B-mode imaging is switched to a voltage for color Doppler imaging. When a B-mode image and a color Doppler image are simultaneously imaged, the voltage HVDD is switched from the voltage for B-mode imaging to the voltage for color Doppler imaging a plurality of times per second.

Accordingly, the intensity varies according to the imaging mode, and appropriately weighted ultrasonic beams can be transmitted from the plurality of transducers 103 to the subject.

An echo of the ultrasonic beam generated in the subject for each transmission is received by the plurality of transducers 103. A reception signal is transferred to the reception unit 105 via the transmission and reception separation unit 104, and reception beamforming processing or Doppler frequency determination processing is implemented according to the imaging mode. Accordingly, focus data or Doppler frequency data is generated for a plurality of reception focuses. The B-mode image or the color Doppler image is generated according to the imaging mode by using data in the image processing unit 106. The generated image is displayed on the display unit 107.

In the above configuration, although for the sake of simplicity of calculation, the case where the resistance value $R_{ref}'$ of the reference resistor 14 and the resistance value $R_{ref}$ of the reference resistor 21 are equal ($R_{ref}$=$R_{ref}'$) is described as an example, the two resistance values may be different.

Although the current control unit 3 controls the attenuation degree of the amplitude control voltage according to the sum of the amplification factors n of the NMOS transistors 18a to 18n that are turned on among the switches 19a to 19n, the same effect can be obtained even when the resistance values of the reference resistor 14 and the resistors 11 and 10 of the reference voltage generation unit 1 are variable.

Further, the above embodiment merely shows one embodiment, and the invention is not limited as long as the amplitude control voltage can be generated from a reference current having a linear relationship with the power supply voltage.

In the configuration described above, the number of the transmission circuit unit 102 and the transmission and reception unit 104 is the same as that of the plurality of ultrasonic transducers 103. The number of the amplitude control voltage generation unit 100 may be the same as the number of the transmission circuit unit 102, or one amplitude control voltage generation unit 100 may be disposed for a plurality of transmission circuit units 102 when the plurality of transducers 103 are driven at the same amplitude.

Whether the transmission unit 120 is disposed on an ultrasonic probe side or on a main body side will be described in fourth and fifth embodiments.

Second Embodiment

An ultrasonic imaging apparatus according to a second embodiment will be described. In the first embodiment described above, a drive signal whose voltage waveform changes between zero and a positive voltage $V_{out}$ is generated. In the second embodiment, a drive signal whose voltage waveform changes in three values including a negative voltage $V_{OUTL}$, a positive voltage $V_{OUTH}$, and a zero level is generated. Accordingly, a positive and negative symmetric waveform can be generated, and THI imaging using pulse-in version can be performed.

In the ultrasonic imaging apparatus according to the second embodiment, the same components as those of the ultrasonic imaging apparatus according to the first embodiment are denoted by the same reference numerals and the description thereof is omitted, and a configuration different from that of the first embodiment will be described below.

In the second embodiment, the variable voltage power supply 121 outputs a positive voltage and a negative voltage. The amplitude control voltage generation unit 100 generates two types of amplitude control voltages: a positive-side amplitude control voltage and a negative-side amplitude control voltage. The transmission circuit unit 102 reduces an absolute value of the positive voltage output from the variable voltage power supply 121 to a value corresponding to the positive-side amplitude control voltage, reduces an absolute value of the negative voltage to a value corresponding to the negative-side amplitude control voltage, and generates a drive signal with the positive voltage after reduction as a positive-side amplitude and the negative voltage after reduction as a negative-side amplitude.

FIG. 6 shows a specific configuration of the transmission unit 120 of the ultrasonic imaging apparatus according to the second embodiment. As in the first embodiment, the transmission unit 120 includes the amplitude control voltage generation unit 100 and the transmission circuit unit 102. The variable voltage power supply 121 includes a variable voltage power supply 121a that supplies a positive voltage and a variable voltage power supply 121b that supplies a negative voltage.

The amplitude control voltage generation unit 100 includes the reference voltage generation unit 1 and the voltage-current conversion unit 2 similar to those in the first embodiment, a current control unit 3a and a positive-side current-voltage conversion unit 4a that perform positive-side amplitude control, and a current control unit 3b and a negative-side current-voltage conversion unit 4b that perform negative-side amplitude control. The positive-side current control unit 3a and the positive-side current-voltage conversion unit 4a have the same configuration as the current control unit 3 and the current-voltage conversion unit 4 of the first embodiment, and generate a positive-side amplitude control voltage. The negative-side current control unit 3b and the negative-side current voltage conversion unit 4b have substantially the same configuration as the current control unit 3 and the current-voltage conversion unit 4 of the first embodiment, but generate a negative-side amplitude control voltage.

That is, the amplitude control voltage generation unit 100 divides an output of the voltage-current conversion unit into the current control unit 3a that performs the positive-side amplitude control and the current control unit 3b that performs the negative-side amplitude control, and generates the positive-side amplitude and the negative-side amplitude individually by the current voltage conversion units 4a and 4b. Here, the reference voltage generation unit 1 and the voltage-current conversion unit 2 are disposed in common without being distinguished between positive and negative, and the negative-side current control unit 3b generates a negative-side amplitude control voltage using the reference current $I_0$ same as the positive side.

In addition to a positive-side amplitude control unit 5a and a positive-side drive circuit unit 6a, the transmission circuit unit 102 includes a negative-side amplitude control unit 5b and a negative-side drive circuit unit 6b connected to the negative variable voltage power supply 121b. The positive-side amplitude control unit 5a and the negative-side amplitude control unit 5b are independently input with the positive-side amplitude control voltage and the negative-side amplitude control voltage. A positive-side drive voltage $V_{OUTH}$ signal and a negative-side drive voltage $V_{OUTL}$ signal respectively output from the positive-side drive circuit unit 6a and the negative-side drive circuit unit 6b are input to a common signal line by shifting a phase of a peak position of a pulse. Thus, a drive signal whose waveform changes between the negative voltage $V_{OUTL}$ and the positive voltage $V_{OUTH}$ is generated. The drive signal is supplied to the transducer 103 to drive the transducer 103. Accordingly, amplitude control that is asymmetrical between positive and negative can be performed, and a drive signal having a complicated waveform can be generated.

A specific circuit configuration example of the amplitude control voltage generation unit 100 is shown in FIG. 7. Circuit configurations of the reference voltage generation unit 1, the voltage-current conversion unit 2, the positive-side current control unit 3a, the positive-side current-voltage conversion unit 4a, and the current mirror circuits (15, 16) that connect the voltage-current conversion unit 2 and the positive-side current control unit 3a to supply the reference current $I_0$ are the same as those of the reference voltage generation unit 1, the voltage-current conversion unit 2, the current control unit 3, the current-voltage conversion unit 4 and the current mirror circuits (15, 16) of FIG. 4 according to the first embodiment.

The negative-side current control unit 3b includes the plurality of NMOS transistors 18a to 18n, and constitutes a current mirror with the PMOS transistor 15. Therefore, although a semiconductor type of the transistor in the negative-side current control unit 3b is different from that in the positive-side current control unit 3a including the NMOS transistor 17 and the plurality of NMOS transistors 18a to 18n having different sizes, the circuit configurations thereof are the same.

The negative-side current-voltage conversion unit 4b has a configuration in which a high withstand voltage PMOS transistor 24 and a reference resistor 25 are connected in series and the negative-side variable voltage power supply 121b is connected to the reference resistor 25. Therefore, although a semiconductor type of the transistor in the negative-side current-voltage conversion unit 4b is different from that in the positive-side current-voltage conversion unit 4a in which the high withstand voltage transistor 20 and the reference resistor 21 are connected, the circuit configurations thereof are the same.

When PMOS transistors 22a to 22n of the negative-side current control unit 3b are turned on and off according to an attenuation degree setting signal output from the transmission control unit 101 by switches 23a to 23n, a current $I_0"$ that is a sum of currents flowing through the turned-on PMOS transistors is output from the PMOS transistors 22a to 22n as an output of the current control unit 3. Therefore, the current $I_0$, which is an input signal to the current control unit 3b, is amplified to the current $I_0'$ and output. When a sum of amplification factors of the PMOS transistors 22a to 22n connected to one or more switches turned on according to the attenuation amount setting signal is m, and a voltage of the negative-side variable voltage power supply 121b is HVSS, the negative-side amplitude control voltage $V_{AMPL}$ is expressed by Formula (8). In the Formula (8), as an example, the negative-side voltage HVSS is equal to an absolute value of the positive-side variable voltage power supply HVDD.

$$V_{AMPL}=HVSS(1-m\times R_2/(R_1+R_2)) \qquad (8)$$

A circuit configuration example of the transmission circuit unit 102 that can output positive and negative voltages is shown in FIG. 8. The positive-side amplitude control unit 5a and the positive-side drive circuit unit 6a are the same as the circuit configurations of the amplitude control unit 5 and the drive circuit unit 6 of FIG. 5 according to the first embodiment. The negative-side amplitude control unit 5b includes a high-voltage PMOS transistor, and the drive circuit unit 6b includes a high withstand voltage PMOS transistor 36, an NMOS transistor 38, and a high withstand voltage NMOS transistor 35 that convert a voltage level.

A transmission control signal output from the transmission control unit 101 is added to the current sources 33 and 37. When outputting an H level, the current source 33 is turned on, and when outputting an L level, the current source 37 is turned on. By repeating the two processing alternately, it is possible to drive the ultrasonic transducer 103 with an H level $V_{OUTH}$ and an L level $V_{OUTL}$. When both the current sources 33 and 37 are turned off, a zero level is output by the load resistor 34. At this time, $V_{OUTH}$ and $V_{OUTL}$ signal levels change in conjunction with the positive and negative amplitude control voltages $V_{AMPH}$ and $V_{AMPL}$. The amplitude control voltage $V_{AMPH}$ is a voltage obtained by attenuating the power supply voltage HVDD by a set attenuation degree, and the amplitude control voltage $V_{AMPL}$ is a voltage obtained by attenuating the power supply voltage HVSS by a set attenuation degree, so that the output signals $V_{OUTH}$ and $V_{OUTL}$ to the transducer 103 also have amplitudes respectively corresponding to the amplitude control voltages $V_{AMPH}$ and $V_{AMPL}$. Even when the voltages of the variable voltage power supplies 121a and 121b are fluctuated, the amplitude control voltages $V_{AMPH}$ and $V_{AMPL}$ are voltages proportional to the power supply voltages HVDD and HVSS, in which the power supply voltage is attenuated by the attenuation degree indicated by the attenuation degree setting signal, so that amplitude control reflecting the magnitude of the power supply voltage and the attenuation degree (weighting) can be performed.

In the above description, the positive-side power supply voltage HVDD and the negative-side power supply voltage HVSS are equal in magnitude. However, in the case of different voltages, the reference voltage generation unit 1 and the voltage current conversion unit 2 may be disposed independently of each other. A transmission circuit whose attenuation degree is constant even when the positive-side power supply HVDD and the negative-side power supply HVSS are different can be provided.

Third Embodiment

Next, a third embodiment will be described. In the first embodiment, the amplitude control voltage $V_{AMP}$ is a voltage value obtained by attenuating the output voltage HVDD of the variable voltage power supply 121 with the set attenuation degree as in Formula (6). However, the voltage $V_{OUT}$ applied to the ultrasonic transducer 103 may be different from the amplitude control voltage $V_{AMP}$ due to an offset voltage generated by the amplitude control unit 5 of the transmission circuit unit 102. For example, in the transmission circuit unit 102 shown in FIG. 5, the H level $V_{OUTH}$ of the output $V_{OUT}$ causes a potential difference between the gate terminal and the source terminal of the NMOS transistor of the amplitude control unit since a current of the current source 33 also flows in the amplitude control unit 5 in a High period. Therefore, when a gate-source voltage is $V_{GS}$, the relationship between $V_{OUTH}$ and $V_{AMP}$ is expressed by Formula (9).

$$V_{OUTH}=V_{AMP}-V_{GS} \qquad (9)$$

Since $V_{GS}$ is a constant voltage that does not depend on the voltage HVDD of the variable voltage power supply, when the power supply voltage HVDD of the transmission circuit unit 102 is small, or when the attenuation degree is set large, $V_{GS}$ cannot be ignored and is output as an error from the set attenuation amount. Therefore, in the third embodiment, as shown in FIG. 9, a fixed current generation unit 7 is provided in the amplitude control voltage generation unit 100, and a current corresponding to the offset voltage $V_{GS}$ is added to the output current from the current control unit 3 to cancel the error in the offset voltage $V_{GS}$.

FIG. 10 shows a specific configuration example. In a circuit configuration similar to that of the amplitude control voltage generation unit 100 in FIG. 4, a fixed offset current source 26 independent of the power supply voltage HVDD of the variable voltage power supply 121 is connected between the switches 19a to 19n of the current control unit 3 and a source of the high withstand voltage NMOS transistor 20 of the current-voltage conversion unit 4 to supply an offset current $I_{off}$. With the above circuit configuration, the amplitude control voltage $V_{AMP}$ is expressed by Formula (10) and the output voltage $V_{OUTH}$ is expressed by Formula (11).

$$V_{AMP}=HVDD(1-n\times R_2/(R_1+R_2))+R_2\times I_{off} \qquad (10)$$

$$V_{OUTH}=HVDD(1-n\times R_2/(R_1+R_2))+R_2\times I_{off}-V_{GS} \qquad (11)$$

Therefore, if the magnitude of the offset current $I_{off}$ is set such that $V_{GS}=R_2\times I_{off}$, the output voltage $V_{OUTH}$ is set as follows:

$$V_{OUTH}=HVDD(1-n\times R_2/(R_1+R_2)).$$

Therefore, the output voltage of the transmission circuit unit 102 can be more accurately attenuated according to the set attenuation degree.

In the above description, the operation of the output voltage $V_{OUTH}$ is described only on the positive side. However, for the output voltage $V_{OUTL}$ of the second embodiment, the offset voltage can be similarly cancelled.

In addition, since the offset voltage $V_{GS}$ may fluctuate due to temperature characteristics and manufacturing variations of the NMOS transistor, when using the variable current source 26 in which the offset current $I_{off}$ changes in conjunction with the fluctuation of the offset voltage $V_{GS}$, the offset voltage $V_{GS}$ can be canceled with higher accuracy and the accuracy of the attenuation degree of the output voltage can be improved.

Fourth Embodiment

As a fourth embodiment, an example of an appearance of an ultrasound system is shown in FIG. 11.

The ultrasonic diagnostic apparatus includes a main frame (apparatus main body) 201, an ultrasonic probe 203, and a cable 202 connecting the main frame 201 and the ultrasonic probe 203. The image display unit 107 is mounted and connected to the main frame 201.

In the present embodiment, the transducer 103 is disposed in the ultrasonic probe 203, and the transmission unit 120 is disposed inside the main frame 201. The transmission unit 120 and the transducer 103 are connected to each other via a wiring inside the cable 202. Therefore, the amplitude control voltage generation unit 100 and the transmission circuit unit 102 are disposed inside the main frame 201.

As described in the first to third embodiments, even when the voltage of the variable voltage power supply 121 is changed, the amplitude control voltage generation unit 100 and the transmission circuit unit 102 of the transmission unit 120 of the present embodiment have a simple circuit configuration that does not need to calculate a voltage value of a drive signal by calculation, and can be attenuated with a set attenuation degree, and thus a circuit scale thereof is small. Therefore, by disposing the amplitude control voltage generation unit 100 and the transmission circuit unit 102 in the main frame 201, it is possible to realize a small main frame.

In the above configuration, since the drive signal attenuated for each of the plurality of transducers 103 is output from the transmission circuit unit 102 of the main frame 201 to the transducer 103 of the ultrasonic probe 203 via the cable 202, a dedicated line is preferably disposed as the cable 202.

Fifth Embodiment

As a fifth embodiment, another example of the appearance of the ultrasound system is shown in FIG. 11.

The ultrasonic diagnostic apparatus of the fifth embodiment includes the main frame (apparatus main body) 201, the ultrasonic probe 203, and the cable 202. The image display unit 107 is mounted and connected to the main frame 201. The transmission unit 120 is disposed in the ultrasonic probe 203.

As described in the first to third embodiments, even when the voltage of the variable voltage power supply 121 is changed, the vibration control voltage generation unit 100 and the transmission circuit unit 102 of the transmission unit 120 of the present embodiment have a simple circuit configuration that does not need to calculate a voltage value of a drive signal by calculation, and can be attenuated with a set attenuation degree, and thus a circuit scale thereof is small. Therefore, it is possible to dispose the transducer 103 in the ultrasonic probe 203, and it is possible to provide the small ultrasonic probe 203.

In addition, since the transmission unit 120 is disposed in the ultrasonic probe 203, the cable 202 only needs to be a cable for a control signal between the transmission control unit 101 and the control unit 122 and a cable for supplying a power supply voltage for the transmission unit 120, and the number of the cable can be reduced, and the size of the cable 202 can be reduced.

In the fourth and fifth embodiments, the transducers 103 disposed in the ultrasonic probe 203 may be arranged in M×N two-dimensional arrays. At this time, as shown in FIG. 13, the transmission circuit unit 102 and a delay circuit that is a part of the reception unit 105 are connected to the transducers 103 as the analog front end circuit 41. Thus, by arranging the transducers 103 in two dimensions and adjusting the transmission focus and the reception focus, a three-dimensional ultrasonic image can be generated.

As shown in FIG. 13, the analog front end circuits 41 for respective transducers 103 arranged by M×N are formed on the same semiconductor substrate and integrated as a beamformer LSI 40 together with a delay control unit of the reception unit 105 and the amplitude control voltage generation unit 100.

At this time, as shown in FIG. 13, the amplitude control voltage generation units 100 may be disposed at ends of rows of the M×N analog front end circuits 41 and supply the amplitude control voltage to the plurality of transmission circuit units 102.

An example of a change in the transmission signal is shown in FIG. 14 as a schematic diagram. From a time t1 in FIG. 14(a) to a time t2 in FIG. 14(b), a center position of the ultrasonic beam to be transmitted is shifted in a row direction, and a transmission signal level for each transducer due to apodization also changes accordingly. In this way, as the transducer is away from the center of the ultrasonic beam to be transmitted, the attenuation degree of the amplitude is set to be gradually increased, and the center position of the ultrasonic beam is moved together with time. This makes it possible to perform ultrasonic beam scanning while reducing the side lobes of the ultrasonic beam.

REFERENCE SIGN LIST 1 reference voltage generation unit
2 voltage-current conversion unit
3 current control unit
3a, 3b current control unit
4 current-voltage conversion unit
4a, 4b current-voltage conversion unit
5 amplitude control unit
5a, 5b amplitude control unit
6 drive circuit unit
6a, 6b drive circuit unit
7 fixed current generation unit
10, 11 resistor
12 operational amplifier (OPAMP)
13, 17, 18a to 18n N-type MOS (NMOS) transistor
14, 25 reference resistor
15, 16, 22a to 22n P-type MOS (PMOS) transistor
19a to 19n, 23a to 23n switch
20 high withstand voltage NMOS transistor
21 high withstand voltage PMOS transistor
24 high withstand voltage PMOS transistor
26 fixed current source
30 PMOS transistor
31, 36 high withstand voltage PMOS transistor
32, 35 high withstand voltage NMOS transistor
33, 37 current source
33 current source
34 load resistor
38 NMOS transistor
40 beamformer LSI
41 analog front end circuit
100 amplitude control voltage generation unit
101 transmission control unit
101a memory
102 transmission circuit unit
103 transducer
104 transmission and reception separation unit
105 reception unit 106 image processing unit
107 display unit
120 transmission unit
121 variable voltage power supply
122 control unit
201 main frame
202 cable
203 ultrasonic probe

The invention claimed is:

1. An ultrasonic imaging apparatus comprising:
a plurality of transducers that transmit ultrasonic waves; and
a transmission unit that supplies drive signals to the plurality of transducers,
wherein the transmission unit includes an amplitude control voltage generation unit and a transmission circuit unit, and the amplitude control voltage generation unit and the transmission circuit unit are connected to a common voltage power supply,
wherein the amplitude control voltage generation unit includes a current mirror circuit including an NMOS transistor and a plurality of NMOS transistors and switches respectively connected to the NMOS transistors,
wherein the amplitude control voltage generation unit receives an output voltage of the voltage power supply and an attenuation degree setting signal instructing an attenuation degree of the drive signal for each of the transducers for weighting for the drive signal, and generates an amplitude control voltage corresponding to a voltage obtained by attenuating the output voltage of the voltage power supply by the attenuation degree based on a sum of the NMOS transistors turned on according to the switches which are switched based on the an attenuation degree setting signal, and
the transmission circuit unit reduces an absolute value of the output voltage of the voltage power supply to a value corresponding to the amplitude control voltage, and generates a drive signal having a predetermined waveform whose amplitude is the voltage after the reduction for each of the transducers.

2. The ultrasonic imaging apparatus according to claim 1, wherein the output voltage of the voltage power supply is variable and is changed according to an imaging mode, which is at least one of a B-mode imaging and color Doppler imaging.

3. The ultrasonic imaging apparatus according to claim 1, wherein the transmission circuit unit and the amplitude control voltage generation unit are disposed for each of the transducers.

4. The ultrasonic imaging apparatus according to claim 1, wherein the amplitude control voltage generation unit includes a reference voltage generation unit that generates a reference voltage from the output voltage of the voltage power supply, a voltage-current conversion unit that converts the reference voltage into a current, and a current-voltage conversion unit that generates the amplitude control voltage by converting the current attenuated by the current control unit into a voltage.

5. The ultrasonic imaging apparatus according to claim 1, further comprising:
a transmission control unit that generates the attenuation degree setting signal for each of the transducers and outputs the signal to the amplitude control voltage generation unit.

6. The ultrasonic imaging apparatus according to claim 1, wherein
the voltage power supply outputs a positive voltage and a negative voltage,
the amplitude control voltage generation unit generates, as the amplitude control voltage, two types of amplitude control voltages, that is, a positive-side amplitude control voltage and a negative-side amplitude control voltage, and
the transmission circuit unit reduces an absolute value of the positive voltage output from the voltage power supply to a value corresponding to the positive-side amplitude control voltage, reduces an absolute value of the negative voltage to a value corresponding to the negative-side amplitude control voltage, and generates the drive signal with the positive voltage after the reduction as a positive-side amplitude and the negative voltage after the reduction as a negative-side amplitude.

7. The ultrasonic imaging apparatus according to claim 4, further comprising:
a current source that adds a current for canceling an offset voltage generated by the transmission circuit unit to a current output from the current control unit.

8. The ultrasonic imaging apparatus according to claim 1, further comprising:
an apparatus main body and an ultrasonic probe connected to the apparatus main body by a cable, wherein
the transducer, the transmission circuit unit, and the amplitude control voltage generation unit are disposed in the ultrasonic probe.

9. An ultrasonic probe comprising:
a plurality of transducers that transmit ultrasonic waves; and
a transmission unit that supplies drive signals to the plurality of transducers,
wherein the transmission unit includes an amplitude control voltage generation unit and a transmission circuit unit, and the amplitude control voltage generation unit and the transmission circuit unit are connected to a common voltage power supply,
wherein the amplitude control voltage generation unit includes a current mirror circuit including an N-type metal-oxide-semiconductor (NMOS) transistor and a plurality of NMOS transistors and switches respectively connected to the NMOS transistors,
wherein the amplitude control voltage generation unit receives an output voltage of the voltage power supply and an attenuation degree setting signal instructing an attenuation degree of the drive signal for each of the transducers for weighting for the drive signal, and generates an amplitude control voltage corresponding to a voltage obtained by attenuating the output voltage of the voltage power supply by the attenuation degree based on a sum of the NMOS transistors turned on according to the switches which are switched based on the an attenuation degree setting signal, and
the transmission circuit unit reduces an absolute value of the output voltage of the voltage power supply to a value corresponding to the amplitude control voltage, and generates a drive signal having a predetermined waveform whose amplitude is the voltage after the reduction for each of the transducers.

10. A transmission apparatus that supplies drive signals to a plurality of transducers that transmit ultrasonic waves, the transmission apparatus comprising:
an amplitude control voltage generation unit, and a transmission circuit unit, wherein the amplitude control voltage generation unit and the transmission circuit unit are connected to a common voltage power supply, wherein the amplitude control voltage generation unit includes a current mirror circuit including an NMOS transistor and a plurality of NMOS transistors and switches respectively connected to the NMOS transistors, wherein the amplitude control voltage generation unit receives an output voltage of the voltage power supply and an attenuation degree setting signal instructing an attenuation degree of the drive signal for each of the transducers for weighting for the drive signal, and generates an amplitude control voltage corresponding to a voltage obtained by attenuating the output voltage of the voltage power supply by the attenuation degree based on a sum of the NMOS transistors turned on according to the switches which are switched based on the an attenuation degree setting signal, and the transmission circuit unit reduces an absolute value of the output voltage of the voltage power supply to a value corresponding to the amplitude control voltage, and generates a drive signal having a predetermined waveform whose amplitude is the voltage after the reduction for each of the transducers.

* * * * *